United States Patent [19]

Sonenberg et al.

[11] Patent Number: 5,219,989
[45] Date of Patent: Jun. 15, 1993

[54] BIFUNCTIONAL PROTEIN FOR THE ISOLATION OF CAPPED MRNA

[75] Inventors: Nahum Sonenberg, Côte St-Luc; Isaac Edery, Chomedey, both of Canada; Michael Altmann, Bern, Switzerland

[73] Assignee: McGill University, Montreal, Canada

[21] Appl. No.: 840,565

[22] Filed: Feb. 24, 1992

Related U.S. Application Data

[63] Continuation of Ser. No. 283,677, Dec. 13, 1988, abandoned.

[51] Int. Cl.$^5$ .......................... C07K 13/00; C12J 1/22
[52] U.S. Cl. ..................... 530/350; 530/413; 435/172.1
[58] Field of Search ............... 530/350, 413; 435/172.1

[56] References Cited

PUBLICATIONS

Sonenbey et al. Proc. Natl Acad. Sci. USA 76(9), pp. 4345–4349 (1979).
Creighton, "Proteins; Structures and Molecular Properties," Freeman & Co.: 1984, pp. 347–348.
Maniatis et al., "Molecular Cloning; A Laboratory Manual" Cold Spring Harbor Lab., New York: 1982, pp. 197–198.

Primary Examiner—Robert J. Hill, Jr.
Assistant Examiner—Shelly J. Guest
Attorney, Agent, or Firm—Dressler, Goldsmith, Shore, Sutker & Milnamow, Ltd.

[57] ABSTRACT

A protein comprising at least a first functional site having the ability to bind the cap structure of mRNA and a second functional site having the ability to bind a solid support matrix in such a manner as to allow the first functional site to be immobilized and still remain functionally accessible to interact with the cap structure of mRNA. Also within the scope of the present invention is a method for generating a cDNA library mostly containing full-length cDNAs. The method comprises the incubation of a mixture comprising mRNA:cDNA hybrids with 1) a single strand RNA specific nuclease and 2) the above-mentioned protein. The resulting mixture is then passed through a column comprising a support matrix having the ability to bind the second functional site of the above-mentioned protein in order to selectively bind complete mRNA:cDNA hybrids. The mRNA:cDNA hybrids are then competitively eluted with a cap analog and full-length cDNA strands are separated and recovered. The present invention also includes a method for purifying capped mRNA using the above-mentioned protein. The process comprises the incubation of a mixture containing mRNA with the above-mentioned protein, passing the resulting mixture through a column comprising the support matrix having the ability to bind to the second functional site of the above-mentioned protein in order to selectively bind capped mRNAs, and competitively eluting the capped mRNAs with a cap analog.

4 Claims, 1 Drawing Sheet

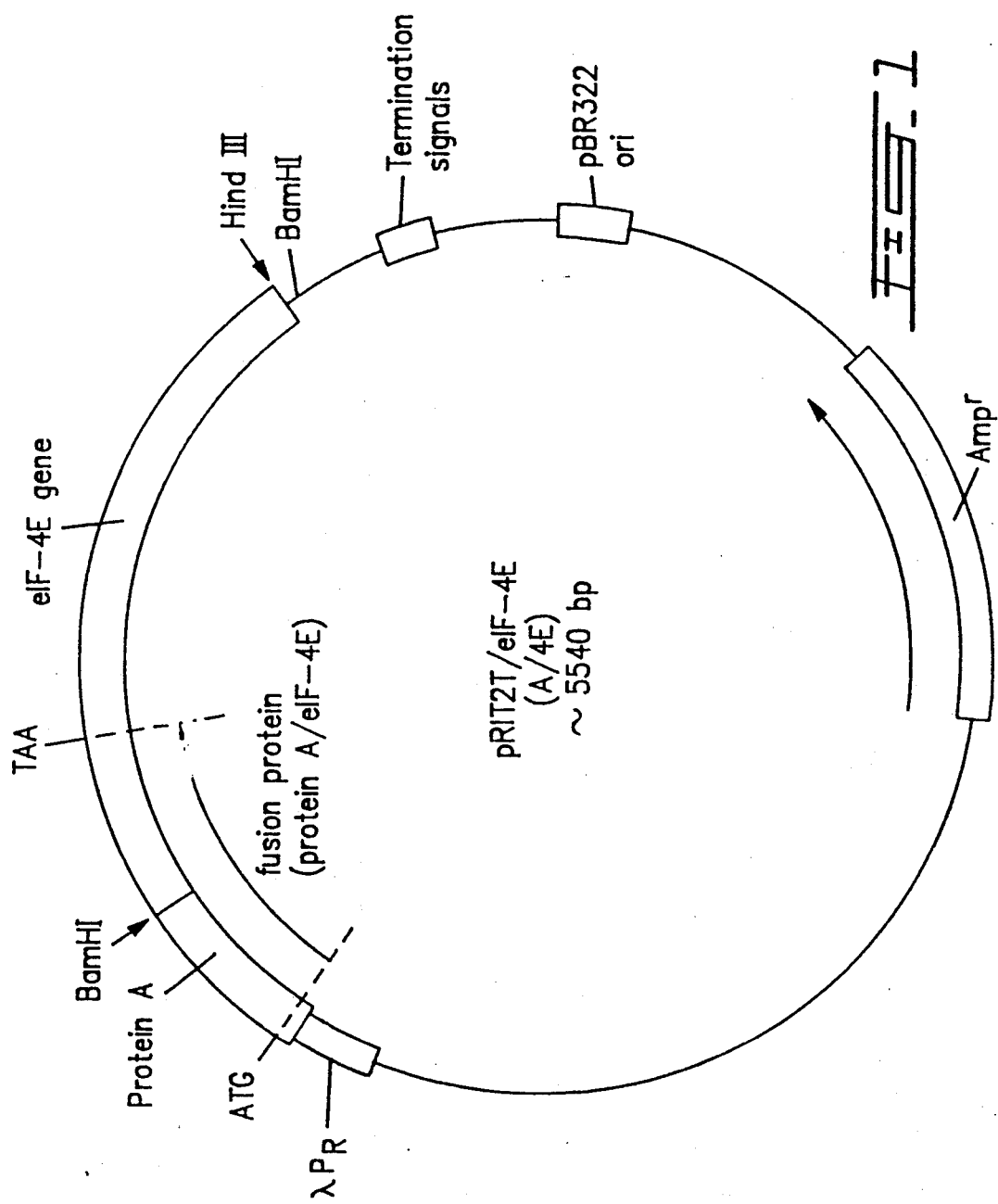

BIFUNCTIONAL PROTEIN FOR THE ISOLATION OF CAPPED MRNA

This application is a continuation, of application Ser. No. 07/283,677, filed Dec. 13, 1988, now abandoned.

BACKGROUND OF THE INVENTION

Complementary DNA contains the information coding for the synthesis of proteins. The ability to generate complementary DNA (cDNA) libraries is one of the most fundamental procedures in contemporary molecular biology. Research involving the use of cDNA libraries has already led to significant breakthroughs in our understanding of cancer, AIDS and numerous other medical concerns. Consequently, there is a rapidly expanding commercial interest in this procedure because of its enormous current and future potential applicability. For example, a growing number of companies are marketing "ready made" cDNA libraries or kits which simplify the task of preparing a cDNA library.

While the procedures for generating cDNA libraries are being continuously modified and improved, there are serious drawbacks in the current methods that have not been adequately addressed. As a result, cDNA cloning is generally inefficient, making it both cumbersome and most unfortunately very time consuming.

In standard methods currently used for the preparing of cDNA libraries, the mRNA in the cell is isolated by virtue of the presence of a polyadenylated tail present at its 3' end which binds to a resin specific for this structure (oligo dT-chromatography). The purified mRNA is then copied into cDNA using the enzyme reverse transcriptase, which starts at the 3' end of the mRNA and proceeds towards the 5' end. Second strand synthesis is then performed. Linkers are added to the ends of the double stranded cDNA to allow for its packaging into virus or cloning into plasmids. At this stage, it is in a form that can be propagated, the sum of which is termed the cDNA library.

Unfortunately, the major problem with the actual technology is that the majority of the cDNAs present in any given library are not full-length because the reverse transcriptase enzyme in the majority of cases does not make a complete copy of the mRNA. Obviously, this creates serious problems, especially if one takes into account the fact that the efficiency of copying is inversely proportional to the length of the mRNA. This results in the majority of the genetic information in a cDNA library having an overabundance of incomplete pieces.

Hence, an incomplete or non full-length cDNA usually does not have the entire genetic blueprint required to make a functional protein and is therefore of limited scientific value. Usually, investigators must perform many rounds of isolation (screenings) and construct a "full-length" cDNA from the accumulated pieces. Consequently, valuable time and scientific resources are lost. Obviously, the problem becomes even more acute when long cDNAs are sought. Additionally, some fragments of the desired cDNAs might be so underrepresented in the library that it may be impractical to identify and isolate all the required segments.

Furthermore, in cDNA libraries produced by conventional methods, there is dismal under-representation of sequences close to the 5' end of mRNAs since the reverse transcriptase will usually "fall off" before reaching these sequences. This is unfortunate since there is a growing interest in isolating these 5' proximal sequences, in light of recent studies pointing to the importance of such sequences in regulating gene expression.

Another problem concerning cDNA synthesis is the source and quality of the mRNA used. Using present day technology, the mRNA that is used as a source for cDNA synthesis is purified by its 3' end polyadenylated tail. However, some mRNAs do not possess a 3' end but all mRNAs have a 5' cap structure. Consequently, a cDNA library constructed from this source of mRNA would be more representative of the total genetic information present in the cell. In recent years, unsuccessful attempts have been made to develop antibodies directed against the cap structure of mRNA. The problems usually encountered were related to the insufficient affinity of the antibodies for the cap. This major drawback made it impossible to develop isolation protocols for capped mRNAs.

Therefore, it would be highly desirable to develop a method that would increase the ability of scientists to isolate both full-length cDNA clones and capped mRNA.

SUMMARY OF THE INVENTION

In accordance with the present invention, there is provided a protein useful for the preparation of cDNA libraries mostly containing full-length cDNA clones. The protein can also be used for the isolation of capped mRNA. The protein of the present invention is a multifunctional protein comprising at least two functional sites. The first functional site has the ability to bind the cap structure of mRNA and the second functional site has the ability to bind a solid support matrix in such a manner as to allow said first functional site to be immobilized and still remain functionally accessible to interact with the cap structure of mRNA. Preferably, a protein of the present invention is a bifunctional fusion protein having one functional site that has the ability to bind the cap structure of mRNA from eucaryotic cells and another functional site having the ability to bind to a solid support matrix.

Also within the scope of the present invention is a method for generating a cDNA library mostly containing full-length cDNAs. This method comprises a first step in which a mixture comprising mRNA:cDNA hybrids is incubated with
1) a single-strand RNA specific nuclease; and
2) a multifunctional protein comprising at least a first functional site having the ability to bind the cap structure of mRNA and a second functional site having the ability to bind a solid support matrix.

The mixture is then passed through a column comprising a support matrix having the ability to bind to the second functional site of the protein in order to selectively bind complete mRNA:cDNA hybrids to the matrix. The mRNA:cDNA hybrids are then competitively eluted with a cap analog and the full-length cDNA strands are then separated and recovered. Preferably, the single-strand RNA specific nuclease that is used for incubating the mRNA:cDNA hybrids mixture is $T_1$ nuclease whereas the preferred cap analog is $m^7GDP$.

Also within the scope of the present invention is a method for purifying capped mRNA. This method comprises the incubation of a mixture comprising mRNA with a protein having a first functional site which has the ability to bind the cap structure of mRNA and a second functional site having the ability to bind a solid support matrix. This mixture is then passed through a column comprising a support matrix having the ability to bind to the second functional site of the protein in order to selectively bind capped mRNAs to the matrix. The capped mRNAs are then competitively eluted with a cap analog such as m⁷GDP and thus capped mRNAs are separated and recovered.

In a preferred embodiment of the present invention, the protein used for generating both cDNA libraries containing full-length cDNAs and pure capped mRNAs is a bifunctional protein, preferably a fusion protein of the type protein A/eIF-4E fusion protein.

Finally, the present invention also includes a resin for the purification of proteins having a functional cap binding site, said resin comprising an oxidized cap analog covalently attached to a solid support matrix. Also included is a method for the preparation of the resin for the purification of proteins having a functional cap binding site, said method comprising:

oxidizing a cap-analog to yield a reactive dialdehyde, and;
 covalently attaching said oxidized cap-analog to a solid support matrix.

Therefore, the product of the present invention will allow, through its selective binding of capped mRNA, an improvement in the quality of cDNA libraries. This, in return, will allow the identification of important genes that are not part of present day cDNA libraries. Furthermore, the product of the present invention can be used to purify capped mRNAs selectively in a reproducible manner.

Other advantages of the present invention will be readily illustrated by referring to the following description.

IN THE DRAWING

FIG. 1 represents the pRIT2T/eIF-4E plasmid.

DETAILED DESCRIPTION OF THE INVENTION

The present invention relates to a novel protein useful in construction of full-length cDNA libraries and the isolation of full-length cDNAs.

Essentially, the product of the present invention has to be at least bifunctional in that it must have the ability to bind the cap structure of mRNA while also having the ability to bind a solid support matrix so that the cap binding portion of this protein can be immobilized and still remain functionally accessible to interact with the mRNA cap structure. The resulting product is a multifunctional protein that has the ability to purify capped mRNAs.

Preferably, the product that will be used in the context of the present invention is a genetically engineered fusion protein that can bind both cap structures of mRNA and a molecule attached to a solid support. However, it is to be understood that the product of the present invention is not limited to fusion proteins but intends to cover all genetically engineered multifunctional proteins possessing the ability to bind to both the cap structure of mRNA and a solid support matrix.

In order to fully appreciate the approach used in the context of the present invention, it might be useful to consider that one of the intermediate steps in cDNA synthesis results in a mRNA:cDNA hybrid. When this hybrid is obtained, it is necessary to add an enzyme that specifically degrades single-stranded RNA. If the cDNA is complete or full-length, it will cover the entire mRNA and protect it against degradation. However, if the cDNA is not complete, then that portion of the mRNA which is not protected will be degraded. This will invariably lead to the loss of the 5' cap structure from the remaining mRNA:cDNA hybrid. Thus, the specific isolation of full-length mRNA:cDNA hybrids will occur when using the fusion protein of the present invention that can bind cap structures because only the full-length mRNA:cDNA hybrids will possess a 5' cap structure. The resulting cDNA library will then have full-length clones only and represents an ideal library for cDNA cloning.

Cap structure and cap binding protein

From all the eucaryotic cellular mRNAs that have been analyzed to date, all of these mRNAs have a structural modification at their 5' end termed the cap structure or "cap" which consists of the structure m⁷GpppX, where X can be any nucleotide. Certain proteins or protein portions have the ability to bind the cap structure and are termed cap binding proteins (CBPs). Thus, if an mRNA has a cap structure, then the cap binding protein will specifically bind the cap in a non-covalent fashion. The affinity of the protein for the cap structure is high, readily allowing the specific retention of capped RNAs as opposed to uncapped RNAs.

The product of the present invention requires a portion having the ability to bind the cap structure of mRNA.

Preferably, a 24 kDa cap binding protein (CBP), which is known as eucaryotic initiation factor 4E (eIF-4E) may be used in the context of the present invention. This protein is found in the cytoplasm of all eucaryotic cells including animal, plant and yeast. However, it is to be understood that any protein or protein portion that can specifically bind the cap structure of mRNA can be considered as being a useful part of the present invention.

Solid support matrix binding proteins

The second essential feature of the product of the present invention is that it must possess a portion having an affinity for molecules that could be bound to a solid support matrix. However, the product must be attached to the support matrix in such a manner as to allow the cap binding portion to interact with the cap structure of mRNAs.

For example, staphylococcal protein A that has the ability to bind IgG immunoglobulins could be used in combination with a resin that has IgG antibodies attached to it. Also, it could be possible to use β-galactosidase in conjunction with an anti-β galactosidase antibody resin. In fact, any protein or protein portion that could possibly be linked to a solid support matrix could be used in the context of the present invention.

Therefore, although the present invention will highlight the use of a fusion protein containing both a cap binding protein and a protein having the ability to bind to a solid support matrix, it is to be understood that the present invention is not limited to these types of proteins. In fact, any multifunctional protein possessing the ability to bind both cap structures of mRNA and a solid support matrix could be useful in the context of the present invention.

Process for the obtention of full-length cDNAs

Once a mixture containing mRNA:cDNA hybrids has been obtained through methods generally known to those skilled in the art, it is incubated with a single-strand RNA specific nuclease. Preferably, $T_1$ nuclease (RNase $T_1$ from Aspergillus oryzae), an endonuclease that specifically attacks the 3' adjacent phosphodiester bound GpN, can be used as a single-stranded RNA specific nuclease. The naturally modified $m^7G$ part of the cap structure will not be recognized by this enzyme. The use of RNAse $T_1$ for probing single-strand specific regions is well documented and widely known to those skilled in the art. RNAs $T_1$ will not attack RNA that is hybridized to DNA and it is therefore well suited for the purposes of the present invention. However, it is to be understood that any single-strand RNA specific nuclease could also be used in the context of the present invention.

Thus, if the reverse transcriptase copies the entire length of the mRNA, or if it falls short of a few nucleotides such that there is no unhybridized GpN residue in the corresponding mRNA, RNAse $T_1$, which will only digest unpaired GpN residues, will not degrade the mRNA and as a result, the cap structure will remain covalently bound to the mRNA:cDNA hybrid. If, however, cDNA synthesis was not complete, the single-strand RNA specific nuclease will degrade unpaired RNA and remove the cap structure from the mRNA:cDNA hybrid.

Following nuclease treatment, the mRNA:cDNA hybrids are incubated with the multifunctional protein of the present invention. As a result of this incubation, only those mRNA:cDNA hybrids that have a covalently attached cap structure will bind to the protein of the present invention. By applying the mixture to a resin having a strong affinity with a functional site of the protein of the present invention, all the non-capped containing hybrids, or incomplete cDNAs, will wash through. The bound full-length capped mRNA:cDNA hybrids will then be competitively eluted with a cap analog such as $m^7GDP$.

The resulting purified fraction contains only full-length or near full-length first strand cDNAs which then act as templates for second strand synthesis. The steps for completing the cDNA library are the same as those normally used by those skilled in the art. Essentially, the present invention lies in the fact that a novel step that discards incomplete cDNAs and readily selects for only full-length cDNAs to be present in the cDNA library has been added to standard cDNA preparation procedures.

Affinity resin for purifying cap binding proteins

The selective purification of cap binding proteins or fusion proteins with a functional cap binding site is most efficiently accomplished by affinity chromatography using cap-analogs covalently attached to a solid support matrix. Although several cap-analog resins have been devised, and one is presently available from Pharmacia, a new cap-analog resin that is less expensive, very rapid, and less demanding to prepare than those previously reported forms part of the present invention.

The synthesis of the cap-analog resin is performed in the following manner. A cap-analog, such as $m^7GDP$, is oxidized in the presence of periodate to yield a reactive dialdehyde. Upon incubation of the oxidized cap-analog with adipic-acid dihydrazide agarose (Pharmacia) a hydrazone bond is formed. The hydrazone bond is further stabilized by reductive amination in the presence of sodium cyanoborohydride ($NaBH_3CN$). This results in a cap-analog covalently attached (through a spacer) to a solid support matrix. The binding efficiency is approximately 90% of the input cap-analog and the resin is stable for months at 4° C. The procedure requires minimal steps and all steps are based on simple chemical reactions.

Affinity purification of capped mRNAs

Independent of its use in constructing full-length cDNAs, the protein of the present invention, when used in combination with a suitable binding resin, can be used to purify capped mRNAs. In cDNA synthesis, there are two major advantages of purifying mRNA by the cap structure rather than using the conventional poly A tail purification.

First, not all eucaryotic cellular mRNAs have a poly A tail at their 3' end whereas all mRNAs analyzed to date have a 5' cap structure. Consequently, the source of mRNA purified will be more representative of the entire spectrum present in the cell.

Secondly, by purifying mRNAs by their cap structure, it is possible to minimize the percentage of degraded mRNA molecules that are normally used as substrates for cDNA synthesis. This feature is extremely important because one of the most variable and important criteria in the generation of a good cDNA library is the quality of the mRNA that is used. If an mRNA is partially degraded, it can still be copied by the reverse transcriptase enzyme as long as there is a 3' poly A tail, thereby exacerbating the problem of incomplete cDNA.

However, if mRNA is purified by its cap structure and it is partially degraded (i.e. 3' sequence and poly A tail are not present), it will not be a substrate for oligo(dT) primed reverse transcription. Only mRNAs which have a cap and a poly A tail simultaneously will be a substrate for cDNA synthesis. Invariably, only full-length mRNAs satisfy this criteria and their use will enhance the quality of present day cDNA libraries.

One must bear in mind that the isolation of mRNA is not always related to cDNA synthesis. For example, the in vitro synthesis of mRNA by using the SP6 system (Promega-Biotec) is widely used. However, the ability to generate capped mRNAs is somewhat variable as it pertains to the efficiency of capping. Therefore, a mixed population of capped and uncapped mRNA is synthesized and this mixture could easily be separated using the system of the present invention.

The following example is introduced in order to illustrate rather than limit the scope of the present invention.

EXAMPLE 1

Construction of the protein A/eIF-4E fusion protein

In order to produce the bifunctional protein A/eIF-4E fusion protein, the yeast eIF-4E gene was fused to staphylococcal protein A, by recombinant DNA technology. The eIF-4E gene was placed in front of protein A using Pharmacia vector pRIT2T. This vector allows for the efficient overproduction of a protein A/eIF-4E fusion protein.

Yeast eIF-4E gene

The yeast eIF-4E gene was isolated using the method described in Altmann et al., Molecular and Cell Biology 7 (1987) p. 998. To create the fusion protein, the yeast eIF-4E gene was mutated by site directed mutagenic in order to obtain a unique BamHI restriction site at the translation start codon. The use of BamHI and HindIII enabled the isolation of the entire coding sequence of eIF-4E except for the first amino acid which is lost as a result of mutagenesis.

Protein A

Staphylococcal protein A has the ability to bind IgG immunoglobulins. Protein A was used because the binding constant of protein A to IgG is remarkably high thereby minimizing the loss of fusion protein from the IgG resin. This feature is important because it allows the purification scheme to be repeated with the same material, thereby increasing the cost-effectiveness of the product. Furthermore, IgG and the resin to which it is covalently bound is rather cheap, effective and easy to prepare. Finally, a commercially available gene fusion vector sold by Pharmacia under the name pRIT2T with protein A sequences placed in an appropriate location allows for an easy overproduction of protein A fusion protein.

Introduction of eIF-4E into pRIT2T and transformation of E. coli

The mutated yeast eIF-4E gene described above is subcloned into KS vector (Pharmacia) into BamI-HindIII site and subsequently cut with HindIII. The ends are Klenow repaired, BamHI linkers are then added, and the desired eIF-4E fragment is cut with BamHI and isolated using standard procedures. The pRIT2T vector is then cut with BamHI and the mutated eIF-4E gene is then ligated to the pRIT2T vector and transformed into E. coli N4830-1. The transformation procedures are those generally used by those skilled in the art. The resulting transformed E. coli strain was given the designation A-4E. The plasmid containing the desired eIF-4E fragment was deposited at the American Type Culture Collection (ATCC) and given the accession number 40522. The Plasmid was deposited at ATCC on Dec. 12, 1988. ATCC is located at 12301 Parklawn Drive, Rockville, Md. 20852-1776 in the United States of America.

Expression and isolation of the protein A/eIF-4E fusion protein

The use of the pRIT2T vector allows for the efficient temperature-inducible expression of intracellular fusion proteins in E. coli. Following the manufacturer's (Pharmacia) procedure, the transformed E. coli cells are grown to an O.D.$_{600}$ value of approximately 1.0 at 30° C. The temperature is then raised from 30° C. to 42° C. for 2 hours. The culture is then sonicated in a buffer containing a mild detergent and centrifuged at low speed spin in order to discard cellular debris. The supernatant liquid is then centrifuged at high speed in order to obtain high yields of the fusion protein. This high speed centrifugation step is not part of the procedure described by the manufacturer and was introduced in order to enhance production yields.

The overexpressed protein is then purified to homogeneity by passing the E. coli extract over a cap analog affinity resin of the type described above such as m$^7$GDP-agarose. Only the fusion protein binds the cap-analog resin because of its affinity for caps and the other contaminating proteins are removed by washing the affinity resin with low salt containing buffer.

The bound fusion protein is then specifically eluted with saturating amounts of a cap analog such as m$^7$GDP, which competes for cap specific binding sites on the fusion protein. The excess m$^7$GDP present with the purified fusion protein is removed by dialysis to yield the fusion protein that can bind cap structures. Approximately 2 to 3 milligrams of pure fusion protein can be obtained for each liter of culture media. The fusion protein thus obtained has proven to be stable for several months at 4° C., apart from being easily overproduced and purified by simple and inexpensive methods.

Solid support matrix used for immobilization of the fusion protein

In order to immobilize the fusion protein of the present invention, it is necessary to use a resin that has an IgG antibody attached to it. This allows for the specific retention of the fusion protein through its protein A portion, thereby allowing the eIF-4E portion to be free to interact with cap mRNAs. Resins of that type are presently available commercially but it was found that the commercially available resins especially those sold by Pharmacia were contaminated with nucleases that degrade mRNA, thereby making it impossible to isolate good quality mRNA. For the purposes of the present invention, a resin synthesized using IgG antibodies obtained from ICN and Affigel-10 resin from Bio-Rad has been used. The column has been found to be stable for at least several months at 4° C.

We claim:

1. A protein A/eIF-4E fusion protein for the purification of capped mRNA in affinity chromatography, which comprises at least a first functional site having the ability to bind a solid support matrix in such a manner as to allow said first functional site to be immobilized and still remain functionally accessible to interact with the cap structure of mRNA.

2. The protein of claim 1, wherein the first functional site has the ability to bind the cap structure of mRNA from eucaryotic cells.

3. The protein of claim 1, wherein the first functional site is the functional site of eIF-4E.

4. The protein of claim 1, wherein the second functional site is the functional site of protein A having an affinity for IgG antibodies.

* * * * *